(12) United States Patent
Cakic et al.

(10) Patent No.: US 11,980,387 B2
(45) Date of Patent: May 14, 2024

(54) CUTTING TOOL FOR THE VERTICAL INCISION OF A TENDON

(71) Applicant: MEDACTA INTERNATIONAL SA, Castel San Pietro (CH)

(72) Inventors: Luka Cakic, Castel San Pietro (CH); Francesco Siccardi, Castel San Pietro (CH); Sascha Berberich, Castel San Pietro (CH); Riccardo Lucchini, Castel San Pietro (CH); Gianluca Parisi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 350 days.

(21) Appl. No.: 17/275,136

(22) PCT Filed: Aug. 21, 2019

(86) PCT No.: PCT/IB2019/057034
§ 371 (c)(1),
(2) Date: Mar. 10, 2021

(87) PCT Pub. No.: WO2020/053684
PCT Pub. Date: Mar. 19, 2020

(65) Prior Publication Data
US 2022/0031349 A1    Feb. 3, 2022

(30) Foreign Application Priority Data

Sep. 13, 2018   (IT) .......................... 102018000008555

(51) Int. Cl.
*A61B 17/3209*   (2006.01)
*A61B 17/00*   (2006.01)

(52) U.S. Cl.
CPC .... *A61B 17/3209* (2013.01); *A61B 17/00008* (2013.01); *A61B 2017/00455* (2013.01); *A61B 2017/00969* (2013.01)

(58) Field of Classification Search
CPC .......... A61B 17/3209; A61B 17/00008; A61B 2017/00455; A61B 2017/00969;
(Continued)

(56) References Cited

U.S. PATENT DOCUMENTS

| 5,026,385 A | 6/1991 | Schutte et al. |
| 5,282,816 A | 2/1994 | Miller et al. |

(Continued)

FOREIGN PATENT DOCUMENTS

| DE | 102011109715 A1 | 2/2013 |
| EP | 0470903 A1 | 2/1992 |

OTHER PUBLICATIONS

International Search Report and Written Opinion for International Application No. PCT/IB2019/057034 dated Nov. 15, 2019, 12 pages.

*Primary Examiner* — Brooke Labranche
(74) *Attorney, Agent, or Firm* — Meunier Carlin & Curfman LLC

(57) ABSTRACT

A cutting tool for the vertical incision of tendons comprising a shaft extending along a longitudinal axis, having a distal end and a proximal end, and a cutting head, located close to said distal end, having a plurality of blades. The cutting head lies on a plane parallel to the longitudinal axis of the shaft and is connected to the latter by a coupling inclined with respect to the longitudinal axis by an angle from 10° to 20°, preferably of 15°.

10 Claims, 4 Drawing Sheets

(58) Field of Classification Search
CPC .. A61B 2017/0046; A61B 2017/00738; A61B 17/320016
See application file for complete search history.

(56) References Cited

U.S. PATENT DOCUMENTS

| | | | | |
|---|---|---|---|---|
| 5,391,169 | A | * | 2/1995 | McGuire ................ A61B 17/15 606/86 R |
| 6,283,960 | B1 | | 9/2001 | Ashley |
| 2012/0283793 | A1 | * | 11/2012 | Burroughs, III ... A61B 17/1767 606/86 R |

* cited by examiner

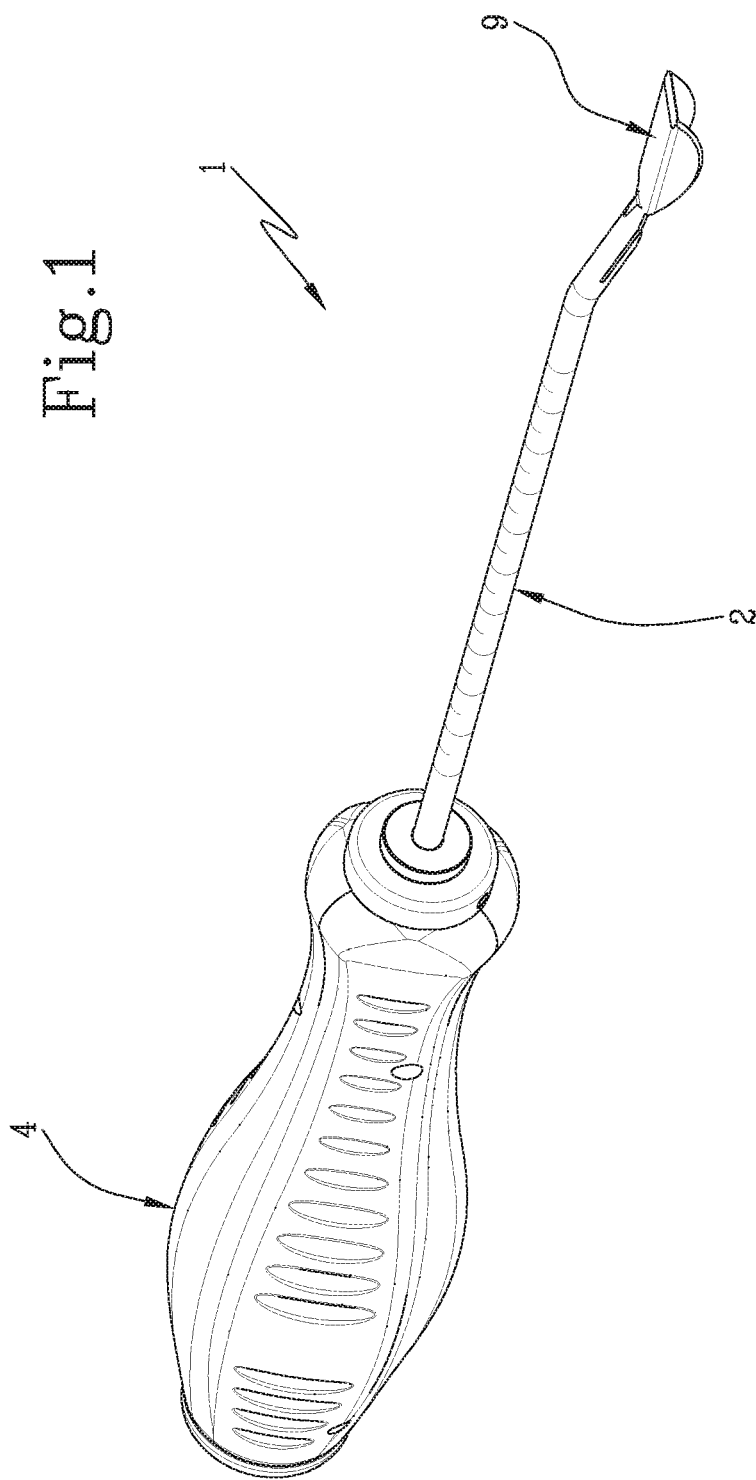

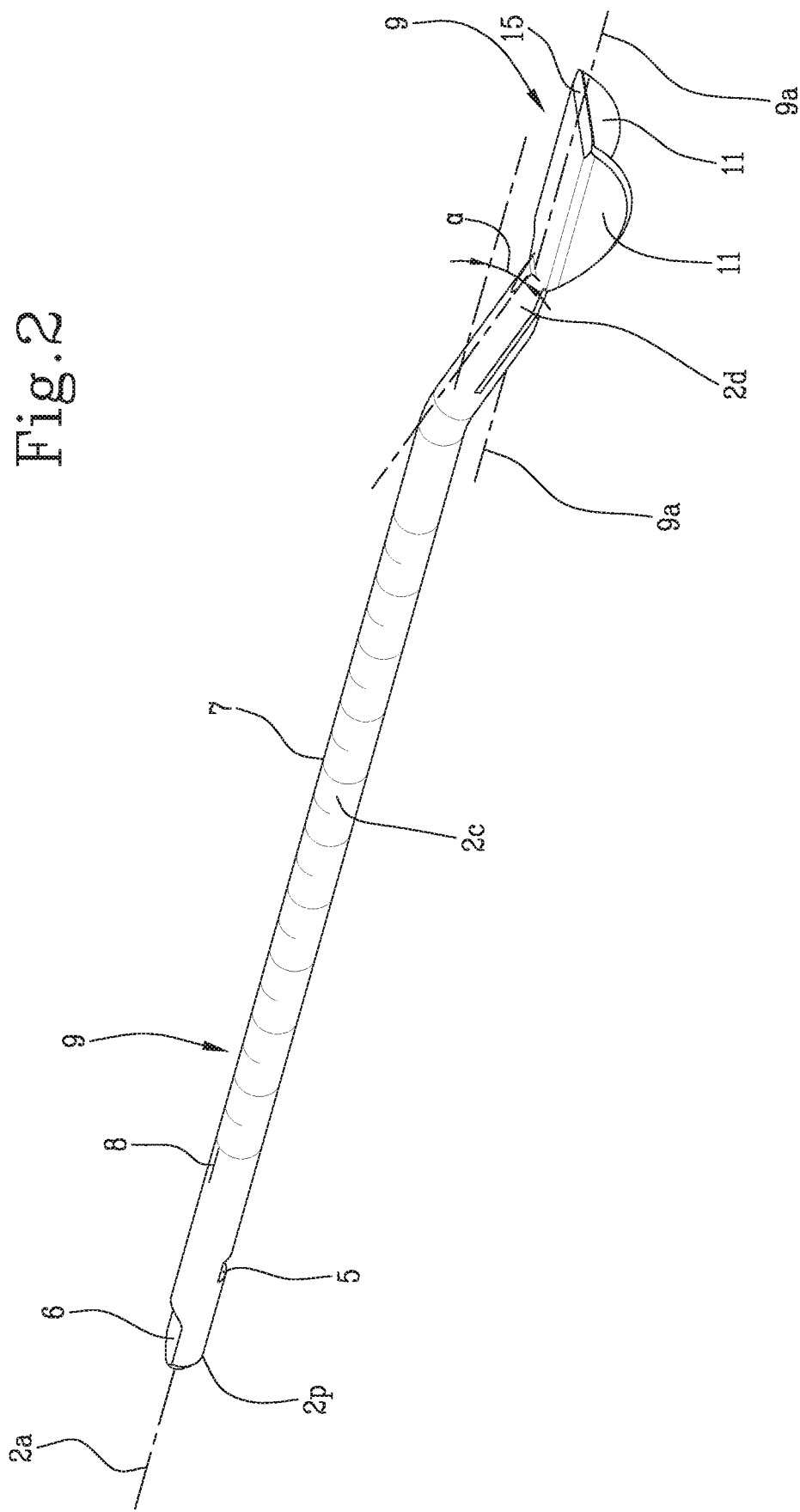

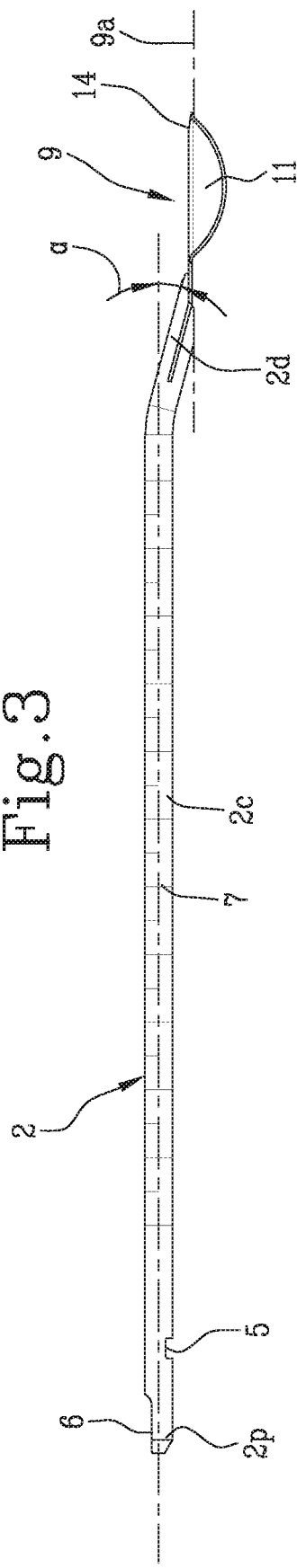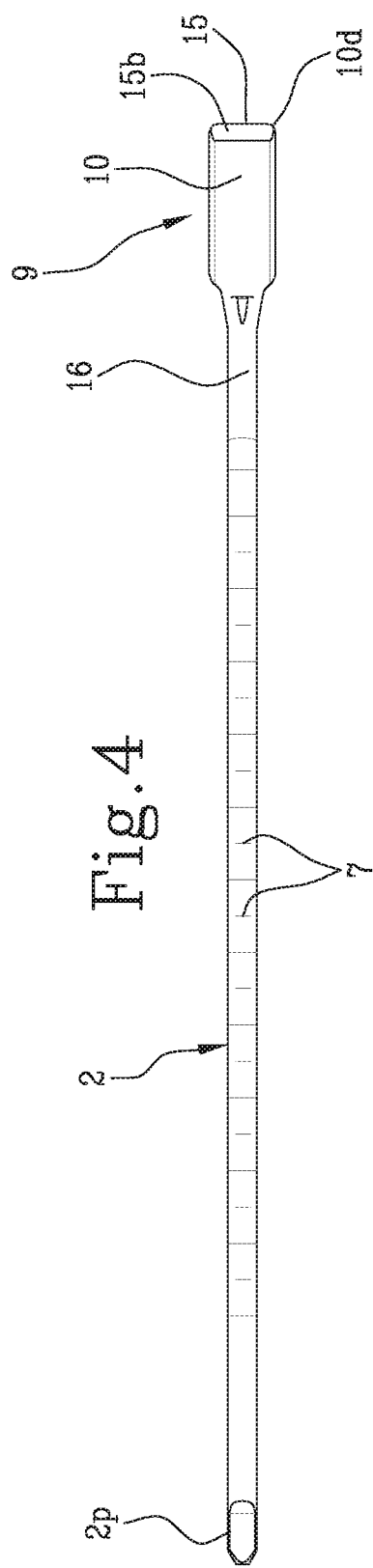

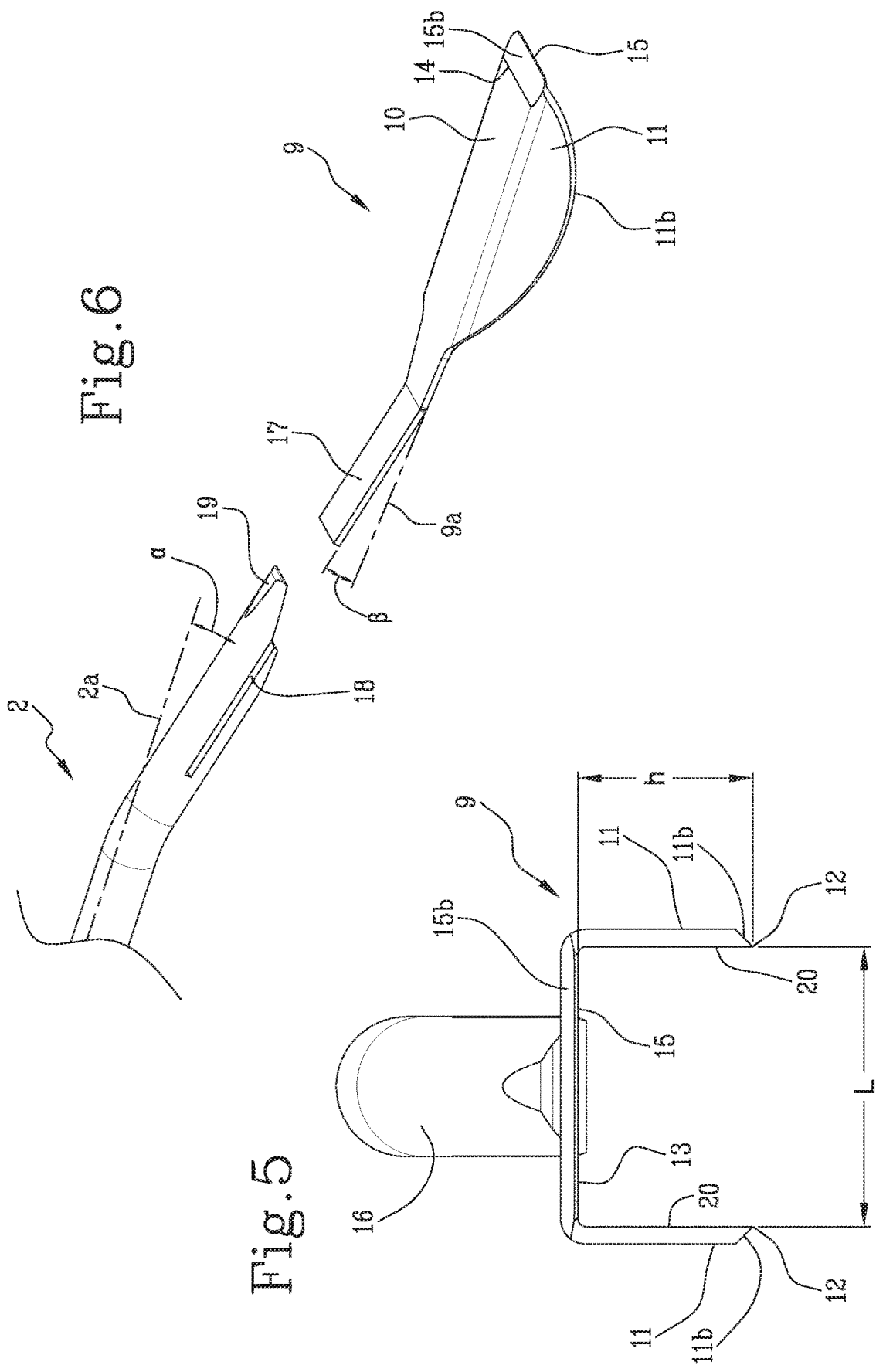

CUTTING TOOL FOR THE VERTICAL INCISION OF A TENDON

SCOPE

The present invention concerns a cutting tool for the vertical incision of a tendon.

PRIOR ART

The cutting tool that is the subject of the present invention is intended for the vertical subcutaneous incision of the quadriceps tendon, which, as is known, offers considerable benefits for the reconstruction of the cruciate ligament.

In fact, the quadriceps tendon can attain a larger diameter than others, its harvest site has a low morbidity compared to e.g. the patellar tendon, it has good biomechanical properties and, since it is less prone to strain or deformation, it has a stiffness profile that is preferable for the reconstruction of the knee ligament.

The surgical technique for cutting and removing the quadriceps tendon involves a cutaneous incision above the upper edge of the patella.

After the subcutaneous dissection, the layers of the pre-patellar bursa are longitudinally split to expose the quadriceps tendon.

Afterwards, the tendon is incised with a vertical cutting tool, or tendon knife, of the desired width for the reconstruction of the cruciate ligament. Through the cutaneous incision, the cutting tool for the vertical incision is applied to the tendon in a subcutaneous position and pushed proximally onto the tendon until the desired graft length for the transplant is achieved. Thus, the tendon is not completely transected but incised at the sides.

A second step of the operation involves horizontally cutting the tendon, parallel to the axis of extension of the tendon itself. With this step, the portion of the tendon to be removed is separated from the surrounding soft tissue above and below by means of a second cutting tool. This cutting tool for horizontal incision, also known as a tendon separator, defines the thickness of the tendon/graft to be removed.

Through the cutaneous incision, the cutting tool for horizontal incision or the tendon separator is introduced laterally into the incision of the tendon and subcutaneously pushed along the same length in the proximal direction to horizontally cut the tendon, above and below, along the tendon's direction of extension.

A third step involves the insertion, again subcutaneously, of a third tool (tendon cutter) adapted to transversely detach the proximal end of the tendon, where "proximal" refers to the patient.

Finally, the distal end of the tendon is also transected, and then removed and prepared for use in reconstructing the cruciate ligament.

Specifically, the present invention concerns a cutting tool for the vertical incision of the tendon and therefore pertains to the cutting tool used in the first part of the operation.

The known surgical techniques require an open surgical procedure and the tools used make the process of harvesting the tendon itself difficult.

Although some of the most modern techniques offer subcutaneous solutions, they still present difficulties because of the design and the methods of using the tool. Some of the disadvantages found in the tools currently used include unstable cutting tips that lead to uncontrolled and dimensionally inaccurate collections. Other tools, on the other hand, have cutting heads with a greater resistance to cutting due to the rectangular geometry of the cutting edges.

The purpose of the present invention is to present a cutting tool for the vertical incision of a tendon that overcomes the drawbacks of the prior art described above.

One of the purposes of the present invention, in fact, is to propose a cutting tool for the vertical incision of a tendon that is minimally invasive, and that ensures a cut in complete safety for the patient without any damage to the surrounding soft tissue.

Moreover, the purpose of the present invention is to propose a cutting tool for the vertical incision of a tendon that is easy for the surgeon to use and that allows a fast, safe, stable and precise cut, despite the surgical site's not allowing the surgeon good visibility.

Another purpose of the present invention is to propose a cutting tool for the vertical incision of a tendon that allows the easy harvesting of the tendon itself as well as preserving the cosmetic aspect after surgery.

These and other purposes are substantially attained by a cutting tool for the vertical incision of a tendon as described in one or more of the accompanying claims.

SUMMARY

In particular, according to a first aspect, the present invention concerns a cutting tool for the vertical incision of tendons.

Preferably, a shaft extending along a longitudinal axis with a distal end and a proximal end is envisaged.

Preferably, the cutting tool also comprises a cutting head, located near said distal end, having a plurality of blades.

Advantageously, the cutting head lies on a plane parallel to the longitudinal axis of said shaft and is connected to the latter by a coupling inclined with respect to the longitudinal axis by an angle of 10° to 20°, preferably of 15°. The lying plane of the cutting head is staggered and parallel to the lying plane of the shaft.

The cutting head, in use, is preferably located below the longitudinal axis of the shaft.

Said cutting head preferably comprises a base plate from which two semicircular (or rounded) lateral blades project, extending along planes parallel to each other and orthogonal to said base plate, and an upper blade, orthogonal to said lateral blades, arranged along an upper edge of the base plate of the cutting head.

Preferably, the semicircular lateral blades and the upper blade each have beveled edges.

In use, the cutting head preferably has an inverted U-shaped cross-section.

The shaft is preferably integral with said cutting head.

The shaft can preferably be coupled to a gripping handpiece to facilitate the surgeon's grip.

The shaft preferably has a notch for stable coupling to the gripping sleeve.

The shaft preferably also has a flat surface to avoid relative rotation between the shaft and the gripping sleeve.

The shaft preferably has a graduated scale along its longitudinal extension.

The shaft preferably has an orientation indicator to aid its correct alignment with the gripping handpiece and the correct insertion of the tool into the surgical site.

Additional features and advantages will emerge in greater detail in the description of a preferred, but not exclusive, embodiment of a cutting tool for the vertical incision of a tendon, according to the present invention and the dependent claims.

BRIEF DESCRIPTION OF THE DRAWINGS

The present invention will be made clearer by the following detailed description, with reference to the attached drawings provided by way of example only, wherein:

FIG. 1 shows a perspective view of a cutting tool for the vertical incision of a tendon in accordance with the present invention;

FIG. 2 shows a perspective view of a portion of the cutting tool shown in FIG. 1;

FIG. 3 is a side view of the cutting tool that is the subject of the present invention, as illustrated in FIG. 2;

FIG. 4 is a top view of the cutting tool that is the subject of the present invention, as illustrated in FIG. 2;

FIG. 5 is a frontal view of the cutting tool that is the subject of the present invention, as illustrated in FIG. 2;

FIG. 6 is a partially exploded view of the cutting tool that is the subject of the present invention, illustrated in a production step.

DETAILED DESCRIPTION

In the above figures, the number 1 designates in its entirety a cutting tool for the vertical incision of a tendon, according to the present invention.

In the example shown, the tool 1 is suitable for being used during the performance of surgery in which the quadriceps tendon is removed from its anatomical site to be implanted at another site for the reconstruction of the cruciate ligament.

The cutting tool 1 comprises a shaft 2 that extends along a longitudinal axis 2a and that has a distal end 2d and a proximal end 2p.

The terms "distal" and "proximal" indicate proximity with respect to the surgeon. The "proximal" end is, therefore, the one closest to the surgeon's hand, while the "distal" end is the one furthest from the surgeon's hand. The proximal end 2p can be connected to a gripping sleeve 4 that acts as the handle of the cutting tool 1. Close to the proximal end 2p, the shaft 2 has a notch 5 for the stable coupling of the shaft 2 itself with the locking mechanism of the gripping sleeve 4. In this way, after coupling, axial sliding along the axis 2a between the gripping sleeve 4 and the shaft 2 is prevented.

At the proximal end 2p, moreover, the shaft 2 has a flat-cut surface 6 that couples with an abutment inside the gripping sleeve 4, to avoid relative rotation between the shaft 2 and the gripping sleeve 4 itself around the longitudinal axis 2a.

The shaft 2 has a graduated scale 7 along the longitudinal extension of the lateral surface 2c, so as to have a reference regarding the depth of insertion of the tool into the skin, to know to what depth to make the cut, and to have an indication of the length of the harvesting and, therefore, of the length of soft tissue to be harvested.

Near the proximal end 2p there is also an orientation indicator 8 to aid the correct alignment with the gripping handpiece 4 and the correct insertion of the tool 1 inside the surgical site.

Close to the distal end 2d, the cutting tool 1 also comprises a cutting head 9 having a plurality of blades 11, 15.

Specifically, the cutting head 9 has a flat horizontal base plate 10, the longitudinal axis 9a of which is parallel to the longitudinal axis 2a of the shaft 2.

The cutting head 9 comprises two semicircular or rounded lateral blades 11, extending along planes parallel to each other and parallel to the longitudinal axis 2a. These lateral blades 11 project orthogonally from the flat surface 10 in a vertical direction, downwards in use configuration, as shown in FIGS. 1 and 2.

The two lateral blades 11, with their circular shape, are suitable for the vertical transection of the soft tissue, so as to cut a strip of soft tissue. The semicircular lateral blades 11 have beveled edges 11b.

The distance between the inner faces 20 of the lateral blades 11 defines the width of the desired portion of soft tissue to be collected.

The combination of the rounded design and of the beveled edges 11b of the lateral cutting blades 11 improves the insertion of the blades into the soft tissue. In addition, these design features significantly improve the advancement (and retraction) of the tools during the collection due to the soft tissue's reduced resistance.

The height of the cut is, on the other hand, defined by the height of the lateral blades 11, in particular by the distance between the lower apex 12 of each lateral circular blade 11 and the lower surface 13 of the horizontal base plate 10 of the cutting head 9.

The cutting head 9 also has an upper edge 14 located at the distal end 10d of the base plate 10.

This edge 14 is orthogonal to the circular lateral blades 11. At this edge 14 there is an upper blade 15, which is also orthogonal to the lateral blades 11. The upper blade 15 also has a beveled edge 15b.

The upper blade 15 and its beveled profile facilitate the insertion and advancement of the tool and the stripping of the soft tissue as the tool advances inside the surgical site.

In other words, when placed in the frontal position, the front bevel of the upper blade 15 aids in lifting the soft tissue above the tendon, facilitating the sliding of the tool because the inclination of the blade progressively affects the tendons with less effort from the surgeon.

In section, the cutting head 9 has an inverted U-shape (in use).

The shaft 2 has, in a distal position, a coupling 16 inclined with respect to the longitudinal axis 2a of an angle α from 10° to 20°, preferably of 15°. This coupling 16 connects the shaft 2 to the cutting head 9.

Following the inclination of the coupling 16, to which the cutting head 9 is joined, in use the cutting head 9 is positioned below the longitudinal axis 2a of the shaft 2.

The position and inclination of the cutting head with respect to the longitudinal axis 2a facilitate the insertion and use of the tool on the upper edge of the patella. The position of the shaft 2 and of the cutting head 9 on staggered planes ensures that the shaft does not touch the tendon during cutting.

The cutting head 9 has a projection 17 that is inserted into a slot 18 during the production of the tool itself.

The projection 17 is also inclined with respect to the longitudinal axis 9a of the cutting head 9 by an angle θ having the same width as the above-mentioned angle α, i.e. from 10° to 20°, preferably of 15°.

The two parts are then firmly coupled together, so that the shaft 2 and cutting head 9 are a single indivisible body.

This type of coupling further stabilises the cutting head 9 with the shaft 2. Moreover, as can be seen in FIG. 6 where the cutting head is represented as separated from the shaft as it is before the end of the production process, the shaft 2 has, at the distal end 2d, a nose 19 that increases the stability of the tool itself because it acts as a rigid vertical stop for the cutting head 9 during use, operating precisely at the point of connection between the cutting head 9 and the shaft 2.

In use, the cutting tool 1 is inserted axially into the dedicated handle, or gripping handpiece 4, for axial collection of soft tissue.

The tip of the cutting blade of the tool 1 must be inserted axially into the desired soft tissue for collection.

Once inserted, the cutting tool 1 must be advanced through the soft tissue, so as to laterally cut a strip of soft tissue with a predefined width and height. The tool is advanced to the pre-established depth, which can be controlled through the graduated scale 7 located on the shaft 2.

The semi-circular lateral blades 11 with beveled edges allow better penetration into the soft tissue and less resistance to be encountered in both forward and reverse directions.

The advantages obtained with this tool are better handling and stability of the tool thanks to the single unit design, with the cutting head firmly connected to the shaft.

In addition, the circular shape of the lateral blades improves the cut backwards and forwards through the soft tissues.

The offset position between the shaft and cutting head and the inclination between the coupling and the shaft facilitate the insertion of the tool at the upper edge of the patella.

The distal bevel of the upper blade aids in advancing the tool as a result of its improved capacity for stripping soft tissues.

The tool is, thus, simple to use. The length of surgery is significantly reduced thanks to the greater smoothness of the tool and the easier stripping of the soft tissues.

The tool thus produced and designed improves the stability of cutting by reducing the likelihood of an unacceptable harvesting of the tendon. The rounded/circular blades and beveled edges of the blades increase its capacity for cutting backwards and forwards, thus overcoming the drawbacks encountered in the prior art.

The invention claimed is:

1. A cutting tool for the a vertical incision of tendons comprising a shaft extending along a longitudinal axis, having a distal end and a proximal end and a cutting head, the cutting head being close to said distal end having a plurality of blades, wherein said cutting head is spaced apart from the longitudinal axis of the shaft and a portion thereof lies on a plane parallel to the longitudinal axis of said shaft and is connected to the said shaft by a coupling inclined with respect to the longitudinal axis by an angle from 10° to 20°, wherein said cutting head comprises a base plate from which two semicircular lateral blades project, the semicircular lateral blades extending within planes parallel to each other and orthogonal to the base plate, each semicircular lateral blade having a convex semicircular cutting edge, and wherein an upper edge of said base plate has a linear cutting edge, the linear cutting edge being orthogonal to said semicircular lateral blades.

2. The cutting tool according to claim 1, wherein said cutting head, in a use configuration, is located below the longitudinal axis of the shaft.

3. The cutting tool according to claim 1, wherein said semicircular lateral blades and said linear cutting edge has a beveled edge.

4. The cutting tool according to claim 3, wherein said cutting head has an inverted U-shaped cross-section in a use configuration.

5. The cutting tool according to claim 1, wherein said shaft is integral with said cutting head.

6. The cutting tool according to claim 1, wherein the cutting tool is couplable to a gripping sleeve.

7. The cutting tool according to claim 6, wherein said shaft has a notch for a stable coupling to said gripping sleeve.

8. The cutting tool according to claim 6, wherein said shaft has a flat surface on the proximal end of the shaft matching with a correspondingly shaped hole in the gripping sleeve to prevent the relative rotation between the shaft and the gripping sleeve.

9. The cutting tool according to claim 1, wherein said shaft has a graduated scale.

10. The cutting tool according to claim 1, wherein said shaft has an orientation indicator to aid a correct alignment with a gripping sleeve and a correct insertion of the cutting head into a surgical site.

\* \* \* \* \*